United States Patent [19]

Rudolph et al.

[11] 4,382,898
[45] May 10, 1983

[54] PROCESS FOR THE PRODUCTION OF AROMATIC CARBOXYLIC ACID CHLORIDES

[75] Inventors: Udo Rudolph; Dieter Freitag; Ludwig Bottenbruch; Manfred Schmidt, all of Krefeld, Fed. Rep. of Germany

[73] Assignee: Bayer Aktiengesellschaft, Leverkusen, Fed. Rep. of Germany

[21] Appl. No.: 312,224

[22] Filed: Oct. 19, 1981

[30] Foreign Application Priority Data

Oct. 25, 1980 [DE] Fed. Rep. of Germany ....... 3040295

[51] Int. Cl.$^3$ .............................................. C07C 51/60
[52] U.S. Cl. ............................ 260/544 D; 260/544 B; 260/544 P
[58] Field of Search ............ 260/544 D, 544 B, 544 P

[56] References Cited

U.S. PATENT DOCUMENTS 3,962,326  6/1976  Semler et al. ................... 260/544 K

FOREIGN PATENT DOCUMENTS 2321122 11/1974 Fed. Rep. of Germany .
1127095  9/1968 United Kingdom .

OTHER PUBLICATIONS

Patai, Saul, "*The Chemistry of Acyl Halides*", (1972), p. 36, Interscience, Publ.

Primary Examiner—Natalie Trousof
Assistant Examiner—L. Hendriksen
Attorney, Agent, or Firm—Connolly and Hutz

[57] ABSTRACT

A single-stage process for the production of pure, particularly sulphur-free, aromatic carboxylic acid chlorides by reacting an aromatic carboxylic acid containing from 1 to 3 carboxyl groups or a corresponding mixture of aromatic carboxylic acids with thionyl chloride in the presence of a catalyst, wherein tertiary phosphine oxides or their reaction products with thionyl chloride and/or the acid chloride to be formed are used as catalysts, and the use of the aromatic dicarboxylic acid dichlorides and tricarboxylic acid trichlorides obtained for the production of polycondensates.

3 Claims, No Drawings

PROCESS FOR THE PRODUCTION OF AROMATIC CARBOXYLIC ACID CHLORIDES

This invention relates to a single-stage process for the production of highly pure aromatic carboxylic acid chlorides capable of polycondensation. The process uses thionyl chloride and, as a catalyst, a tertiary phosphine oxide or its reaction product with thionyl chloride and/or the acid chloride formed. The reaction of aliphatic and aromatic carboxylic acids with thionyl chloride is a standard process in preparative organic chemistry for producing the corresponding acid chlorides. Unfortunately, dark-coloured reaction products having a carboxylic acid chloride content of only 96 to 99% by weight are normally obtained. Aromatic dicarboxylic acid dichlorides as impure as these cannot be directly reacted, for example, by the two-phase interface process for the production of high molecular weight polycondensates, such as aromatic polyamides or aromatic polyesters. The presence in them of unreacted or only semi-reacted dicarboxylic acids interferes with the polycondensation reaction, causes undesirable chain termination and gives polymers having terminal carboxyl groups and, in the case of the polyesters, polymers containing additional anhydride structures. In the production of acid chlorides using thionyl chloride and dimethyl formamide as catalyst (cf. German Pat. No. 1,026,750), considerable quantities of dimethyl carbamic acid chloride can be formed as a secondary product, additionally contaminating the product or accumulating in the optionally recycled excess thionyl chloride.

In addition, acid chlorides produced in this way contain sulphur in elemental form and, above all, in bound form, which also has an adverse effect upon the properties of the resulting polycondensate.

In order to obtain colourless dicarboxylic acid dichlorides having a purity of ≧99.9% by this process, the products have to be purified by recrystallisation or distillation. This involves additional outlay and reduces the yield. Distillation is attended by the danger of spontaneous decomposition.

The reaction of thionyl chloride with aromatic mono-, di- and tri-carboxylic acids, in the presence, as catalyst, of a tertiary phosphine oxide or its reaction product with thionyl chloride and/or the acid chloride formed, gives colourless aromatic carboxylic acid chlorides having a COOH-content of ≦0.05% and a total sulphur content of ≦50 ppm, so that they may be used without subsequent purification for the production of colourless, high molecular weight polycondensates.

Accordingly, the present invention provides a single-stage process for the production of pure, particularly sulphur-free, aromatic carboxylic acid chlorides by reacting the corresponding acids with thionyl chloride, which is characterised in that tertiary phosphine oxides or their reaction products with thionyl chloride and/or the acid chlorides formed are used as catalysts. The phosphine oxides and their reaction products used as catalysts in accordance with the invention may remain in the acid chloride without any adverse effect upon the properties of the polycondensate to be produced.

Catalysts active in accordance with the invention are tertiary phosphine oxides generally corresponding to general formula (I) below:

in which $R_1$, $R_2$ and $R_3$ may be the same or different and represent $C_1$-$C_8$-alkyl, $C_6$-$C_{10}$-aryl, $C_7$-$C_{20}$-alkylaryl or arylalkyl. $R_1$, $R_2$ and $R_3$ are preferably $C_6$-$C_{12}$-aryl radicals, such as phenyl or phenyl substituted by $C_1$-$C_4$-alkyl radicals. The hydrocarbon radicals $R_1$, $R_2$ and $R_3$ thus characterised may be additionally substituted, for example by halogen.

Suitable catalysts are triisopropyl phosphine oxide, tributyl phosphine oxide, trihexyl phosphine oxide; triphenyl phosphine oxide, tri-1-naphthyl phosphine oxide, tri-2-biphenylyl phosphine oxide, tri-4-biphenyl phosphine oxide, tris-4-methyl phenyl phosphine oxide, diphenyl-(4-methylphenyl)-phosphine oxide, phenyl-bis-4-methylphenyl phosphine oxide, tribenzyl phosphine oxide, dimethyl benzyl phosphine oxide, methyl diphenyl phosphine oxide, diethyl phenyl phosphine oxide, ethyl phenyl benzyl phosphine oxide and bis-chloromethyl-(3-chlorophenyl)-phosphine oxide.

Triphenyl phosphine oxide is particularly suitable.

According to the invention, the tertiary phosphine oxides corresponding to general formula (I) are generally used in a quantity of from 0.1 to 5.0% by weight and preferably in a quantity of from 0.1 to 1.0% by weight, based on the aromatic acids used.

In principle, it is possible to use any aromatic carboxylic acids. They correspond in particular to formulae (II) to (VII) below:

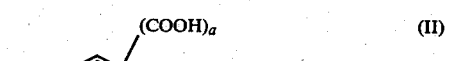

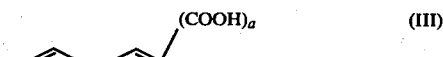

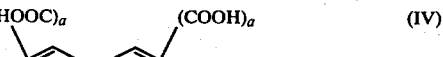

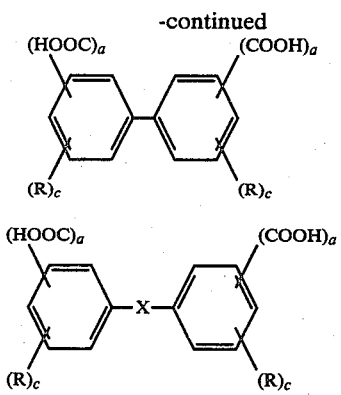

in which R may be a substituent from the group comprising alkyl groups containing from 1 to 6 carbon atoms, halogen-substituted alkyl groups containing from 1 to 6 carbon atoms, alkoxy groups and also the corresponding halogen-substituted alkoxy groups containing from 1 to 6 carbon atoms and halogen atoms, X represents an ether oxygen, a methylene group or isopropylene group, a $C_5$–$C_7$-cycloalkylene radical or a —C=O—group, whilst a is an integer of from 1 to 3 (provided there are not more than 3 COOH groups per molecule), b is an integer of from 0 to 5, c is an integer of from 0 to 4 and d is an integer of from 0 to 3.

Examples of suitable acids are phthalic acid, isophthalic acid, terephthalic acid, mixtures of isophthalic and terephthalic acid, 4,4′-dicarboxy benzophenone, diphenoic acid, 1,4-naphthalene dicarboxylic acid and trimesic acid.

To carry out the process according to the invention, from 1 to 2 moles of thionyl chloride per carboxyl group may be added to the aromatic carboxylic acids following the addition of the catalysts according to the invention and the resulting suspension or solution heated to temperatures of from 50° to 150° C. and preferably to temperatures of from 80° to 100° C.

After the excess thionyl chloride has been distilled off and a vacuum briefly applied at the reaction temperature, a residue of which ≧99.9% by weight consists of aromatic carboxylic acid chloride is obtained.

The process may be carried out either continuously or in batches. In the following Examples all percentages are by weight.

EXAMPLE 1

The following components are introduced into and heated in a 1-liter three-necked flask equipped with a stirrer, thermometer and reflux condenser: 83 g of isophthalic acid, 83 g of terephthalic acid, 357 g of thionyl chloride, and 0.83 g of triphenyl phosphine oxide. The colourless suspension is heated to 60°–80° C. over a period of 30 minutes during which there is a vigorous evolution of HCl and $SO_2$. After about 8 hours, the evolution of gas is over. A pale yellow solution is obtained from which the excess thionyl chloride is removed first at normal pressure and then in vacuo at 100° C.

In addition to the catalyst, the colourless residue contains ≧99.9% of acid chloride, ≦0.05% of COOH, ≦5 ppm of total sulphur and ≦0.05% of $Cl^-$. Yield: 100%.

EXAMPLE 2

210 g of trimesic acid, 267.7 g of thionyl chloride and 1.05 g of triphenyl phosphine oxide give trimesic acid trichloride in the same way as described in Example 1. In addition to the catalyst, the trimesic acid trichloride contains ≧99.9% of acid chloride, ≦0.05% of COOH, ≦50 ppm of total sulphur and ≦0.05% of $Cl^-$. Yield: 100%.

EXAMPLE 3

166 g of isophthalic acid, 261.8 g of thionyl chloride and 1 g of tributyl phosphine oxide give isophthalic acid dichloride in the same way as described in Example 1. In addition to the catalyst, the isophthalic acid dichloride contains ≧99.9% of acid chloride, ≦0.05% of COOH, ≦5 ppm of total sulphur and ≦0.05% of $Cl^-$. Yield: 100%.

EXAMPLES 4 TO 10

166 g of isophthalic acid and 261.8 g of thionyl chloride were successively reacted in the presence of 1 g in each case of triisopropyl phosphine oxide (4), trihexyl phosphine oxide (5), dimethyl benzyl phosphine oxide (6), tribenzyl phosphine oxide (7), methyl diphenyl phosphine oxide (8), ethyl phenyl benzyl phosphine oxide (9) and bischloromethyl-(3-chlorophenyl)-phosphine oxide.

The products all had the same analytical data and were obtained in the same yields as the product described in Example 3.

We claim:

1. A single-stage process for the production of an aromatic carboxylic acid chloride which comprises reacting an aromatic carboxylic acid containing from 1 to 3 carboxyl groups or a mixture of such acids with 1 to 2 mols of thionyl chloride per carboxylic acid group of said aromatic carboxylic acid or mixture thereof at a temperature of from 50° to 150° C. in the presence of a catalytic amount of a tertiary phosphine oxide or the reaction product thereof with thionyl chloride.

2. A process as claimed in claim 1, wherein the tertiary phosphine oxide is a compound corresponding to the formula

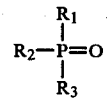

in which $R_1$, $R_2$ and $R_3$ are the same or different and represent $C_1$–$C_8$-alkyl, $C_6$–$C_{12}$-aryl, $C_7$–$C_{20}$-alkylaryl or arylalkyl.

3. Process according to claim 1, wherein the tertiary phosphine oxide is a compound of the formula

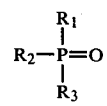

wherein $R_1$, $R_2$ and $R_3$ are $C_6$–$C_{10}$-aryl radicals, such as phenyl or phenyl substituted by $C_1$–$C_4$-alkyl radicals.

* * * * *